United States Patent [19]

Ford

[11] Patent Number: 5,095,977

[45] Date of Patent: Mar. 17, 1992

[54] COUPON HOLDER FOR CORROSION TEST DOWNHOLE IN A BOREHOLE

[76] Inventor: Michael B. Ford, 20407 Sagewood, Parker, Colo. 80134

[21] Appl. No.: 508,026

[22] Filed: Apr. 10, 1990

[51] Int. Cl.⁵ .............................................. E21B 47/00
[52] U.S. Cl. ..................................... 166/113; 422/53; 73/53; 73/86; 166/902
[58] Field of Search .................. 436/6; 422/53; 73/53, 73/86; 166/113, 250, 902

[56] References Cited

U.S. PATENT DOCUMENTS

| | | | |
|---|---|---|---|
| 2,994,778 | 8/1961 | Marsh | 250/106 |
| 3,451,264 | 6/1969 | Kaston | 73/155 |
| 4,483,397 | 11/1984 | Gray | 166/250 |
| 4,501,323 | 2/1985 | Lively et al. | 166/250 |
| 4,603,113 | 7/1986 | Bauer | 436/6 |
| 4,605,065 | 8/1986 | Abercrambie | 166/250 |
| 4,688,638 | 8/1987 | Williams | 166/250 |
| 4,697,465 | 10/1987 | Evans et al. | 73/866.5 |
| 4,768,373 | 9/1988 | Spencer | 73/86 |
| 4,928,760 | 5/1990 | Freitas | 166/902 |

*Primary Examiner*—David L. Lacey
*Assistant Examiner*—Jeffrey R. Snay
*Attorney, Agent, or Firm*—Marcus L. Bates

[57] ABSTRACT

A coupon holder apparatus for measuring the rate of corrosion caused by formation fluid contained downhole in a borehole. The apparatus is useful when used in conjunction with a pumping unit of the type having a pump located at the bottom of a borehole and a sucker rod string extending downhole through a tubing string to actuate the pump. The apparatus has a main body which is connected in the rod string and suspended downhole in the borehole where it is in contact with the well fluids. An axial chamber is formed within the main body and radial ports extend through a sidewall of the main body to communicate the axial chamber with the borehold fluids. A coupon that chemically reacts with the well fluids is mounted within the chamber and is insulated from the interior sidewall of the chamber so that well fluid makes contact with the coupon, and the coupon reacts with the well fluid, to enable the rate of reaction between the coupon and the well fluid to be measured and used as an indication of the rate of corrosion.

15 Claims, 2 Drawing Sheets

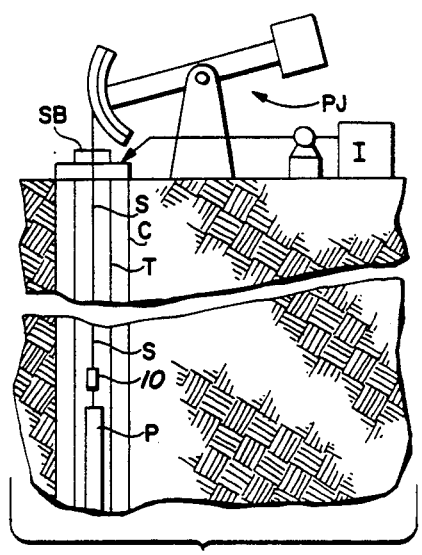
FIG. 1
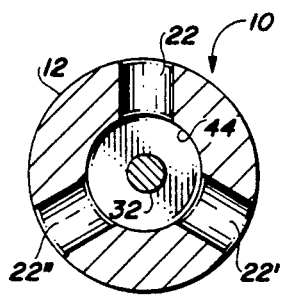
FIG. 3
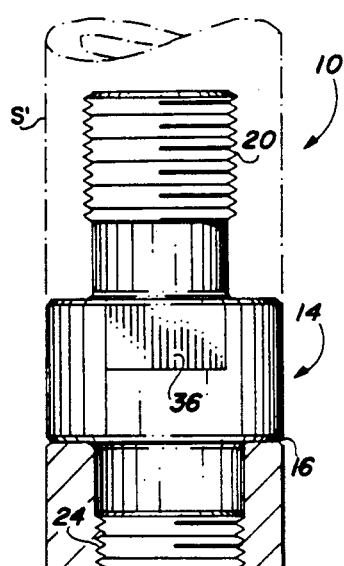
FIG. 2
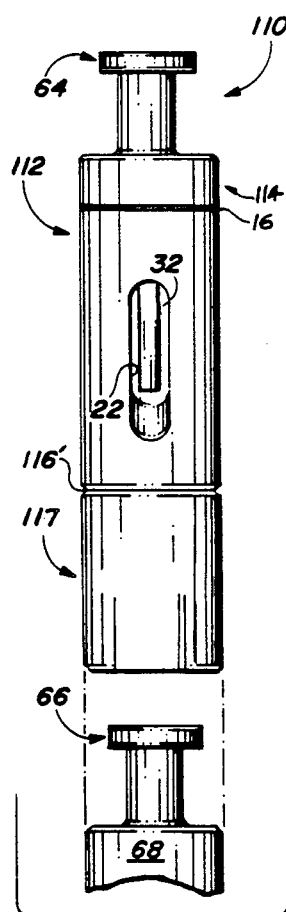
FIG. 7
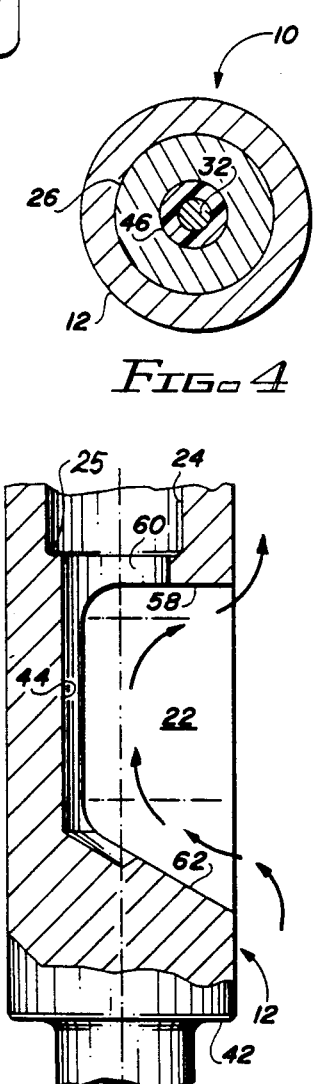
FIG. 6
FIG. 4

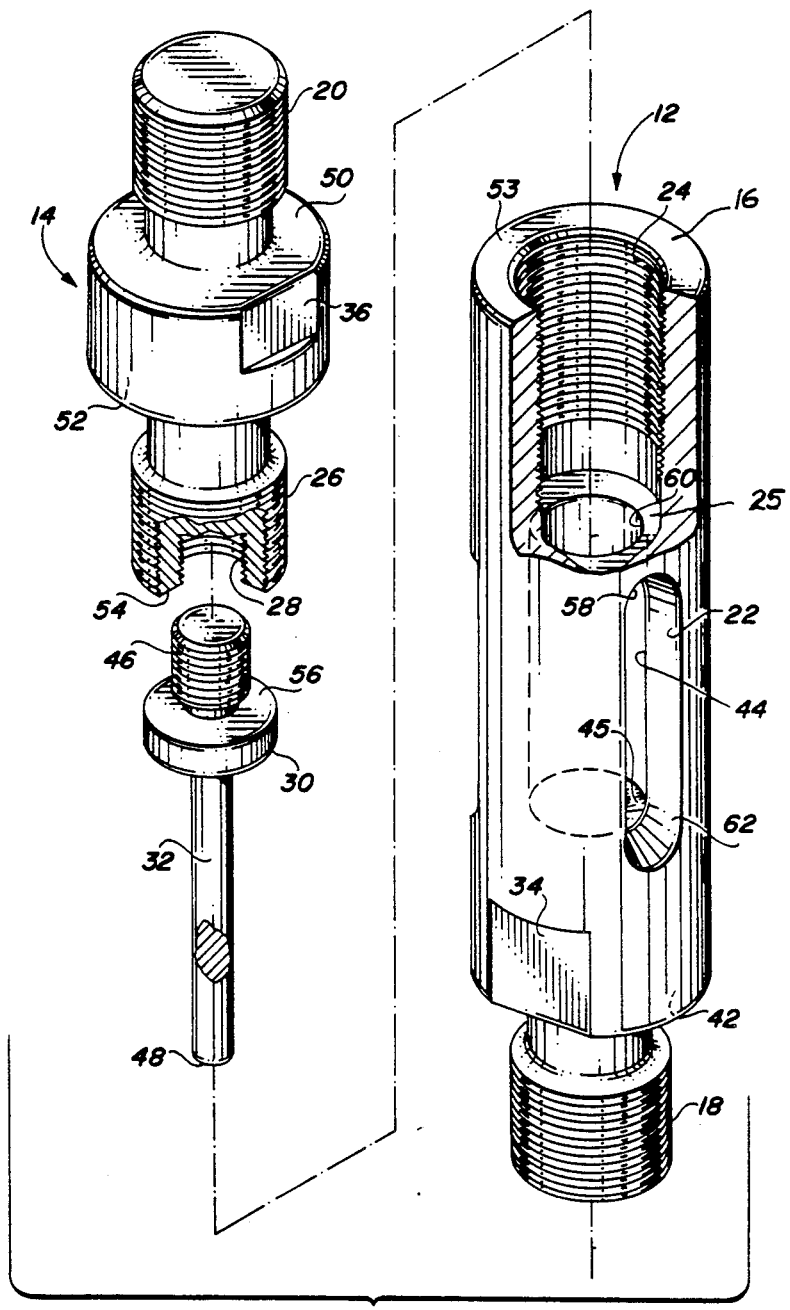
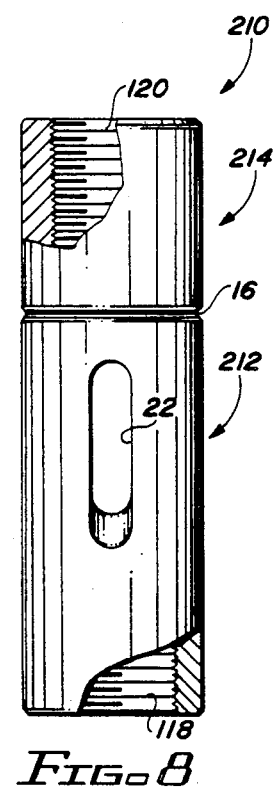
FIG. 5
FIG. 8

5,095,977

COUPON HOLDER FOR CORROSION TEST DOWNHOLE IN A BOREHOLE

BACKGROUND OF THE DISCLOSURE

The reservoir pressure of most oil wells is insufficient to force the formation fluid to free flow from the bottom of the borehole, up the tubing string, and to the surface of the ground. It is therefore necessary to rely upon artificial lift means in order to produce most oil wells. This is usually accomplished with a pumpjack unit having a string of sucker rods extending downhole in a cased wellbore for reciprocating a downhole pump. Apparatus such as this has been used for many years. The well casing, downhole pump, production tubing, and string of sucker rod are all placed in intimate contact with the well fluids.

The well fluids usually are very corrosive and accordingly these expensive mechanical components are subjected to the deleterious effects of the corrosive liquid and gas produced by the oil well. For this reason, from time to time, it is advantageous to treat the borehole with a corrosion inhibiting compound. It would, therefore, be desirable to measure the rate of corrosion that occurs downhole in a borehole in order to enable the reservoir engineer to ascertain the appropriate amount of inhibitor to add to the borehole.

The determination of the rate of corrosion that occurs on the production equipment used downhole in a wellbore is the subject of the present invention.

SUMMARY OF THE INVENTION

This invention is to an apparatus for measuring the rate of corrosion downhole in a borehole. The invention is used to provide data for selecting an appropriate quantity of inhibitor to be added to the borehole at predetermined intervals of time in order to reduce the corrosive action of the well fluids to a minimum.

This invention relates to apparatus for measuring the rate of corrosion that occurs between well components and formation fluid downhole in a borehole. The apparatus comprises a main body that is suspended in well fluids downhole in the borehole. The main body has radial ports leading to an axial chamber within which a special coupon is mounted in insulated relationship respective to the sidewalls that form the chamber. Well fluid is free to flow into and out of the chamber, and thereby react with the coupon, whereby the rate of reaction that occurs between the well fluid and the coupon is a measure of the rate of corrosion that occurs downhole in the borehole.

More specifically, the present invention is used in conjunction with a pumping unit having a pump located downhole in a borehole and a sucker rod string extending downhole through a tubing string to actuate the pump. A coupon apparatus for measuring the rate of corrosion caused by the fluid contained downhole in the borehole is mounted in a special holder therefor, and the holder is connected to the sucker rod string and reciprocates therewith. Radial ports are formed in the holder and communicate with an axial chamber thereof. The coupon is supported within the chamber and free of the walls that form the chamber. Fluid is forced to flow through the radial ports in response to the reciprocatory action of the rod string. The rate of reaction between the coupon and the well fluid is a measure of the rate of corrosion that is occurring downhole in the borehole. This measured rate of reaction provides a means by which the reservoir engineer can calculate the quantity of inhibitor that must be added to the wellbore in order to control the deleterious effect of the well fluids on the production equipment.

A primary object of the present invention is the provision of a means for measuring the rate of corrosion caused by the well fluids respective to the equipment located downhole in a borehole.

Another object of this invention is the provision of an apparatus for holding a coupon downhole in a borehole, such that well fluid flows across the coupon, reacts therewith, and provides a measure of the rate of corrosion downhole in the borehole.

A further object of this invention is to disclose and provide an apparatus for connection to a downhole pump by which the rate of corrosion caused by the well fluid located downhole in a borehole can be determined.

A still further object of this invention is the provision of apparatus connected to the rod string of a pumping unit, said apparatus having a coupon supported therewithin in a manner whereby fluid produced by the pump flows across the coupon and reacts therewith to thereby provide a measure of the rate of corrosion downhole in the borehole.

These and various other objects and advantages of the invention will become readily apparent to those skilled in the art upon reading the following detailed description and claims and by referring to the accompanying drawings.

The above objects are attained in accordance with the present invention by the provision of apparatus fabricated in a manner substantially as described herein.

BRIEF DESCRIPTION OF THE DRAWINGS

FIG. 1 is a part diagrammatical, part schematical, broken, part cross-sectional, side view of a pumping unit having apparatus made in accordance with the present invention associated therewith;

FIG. 2 is an enlarged, side elevational view of part of the apparatus disclosed in FIG. 1, with some parts being removed therefrom, and some of the remaining parts being shown in cross-section;

FIG. 3 is a cross-sectional view taken along line 3—3 of FIG. 2;

FIG. 4 is a cross-sectional view taken along line 4—4 of FIG. 2;

FIG. 5 is a disassembled, perspective view showing some of the details of the apparatus disclosed in the foregoing figures, with some parts being broken away therefrom, and some of the remaining parts being shown in cross-section;

FIG. 6 is an enlarged, fragmentary, longitudinal, cross-sectional view of part of the apparatus disclosed in the foregoing figures;

FIG. 7 is a modification of apparatus made in accordance with the present invention; and, FIG. 8 sets forth another modification of apparatus made in accordance with the present invention.

DETAILED DESCRIPTION OF THE PREFERRED EMBODIMENT

FIG. 1 of the drawings sets forth a pumpjack unit PJ having a string of sucker rod S extending downhole through a tubing string T located within a cased borehole C. The sucker rod string S has apparatus 10 series connected therewithin and made in accordance with the present invention for measuring the rate of corrosion downhole in the borehole. The sucker rod string is connected to a downhole pump P of usual construction. From time to time, inhibitor I is pumped into the casing annulus in order to inhibit the deleterious effects of the corrosive formation fluid to the equipment in the wellbore.

FIG. 2, together with other figures of the drawings, shows the details of apparatus 10, which is a corrosion test coupon holder, made in accordance with the present invention. Apparatus 10 includes a main body comprised of lower body member 12 and upper body member 14. The upper and lower body members are threadedly fastened together and are joined together at interface 16. Lower threaded connection 18 is diametrically opposed to upper threaded connection 20.

Circumferentially spaced, radially arranged, fluid flow ports 22 preferably are spaced 120 degrees apart and provide egress and ingress of well fluid to and from the interior of apparatus 10, as will be more fully appreciated later on in this disclosure.

Numeral 24 is a female thread formed within the lower body member 12. Annular shoulder 25 is spaced from the upper member. Male thread 26 is formed on the illustrated extension of the upper body member 14. The threaded areas 24 and 26 join the lower and upper body members 12 and 14 together in a removable manner. Numeral 28 indicates a female thread that threadedly receives a coupon insulator 30. A coupon 32, of cylindrical configuration, is supported by the insulator 30. The coupon 32 is spaced from all metal parts of the upper and lower body members 14 and 12. The upper marginal end of the coupon is fixed to the insulator by any convenient means, such as threads, cementing, or interference fit. The central axis of the coupon coincides with the central axis of insulator 30, coupon holder, and main body. The insulator 30 has a boss at the coupon receiving end thereof. The boss of insulator 30 has opposed faces that abut annular shoulders 25 and 54 and thereby lock the insulator into the illustrated position of FIGS. 2 and 5.

Wrench flats 34 and 36, respectively, are provided on marginal lengths of the lower and upper bodies 12 and 14, respectively. A neck 38 extends from the last thread 40 of the lower threaded connection 18 to an annular shoulder 42. A chamber 44, the details of which are more fully disclosed in FIGS. 3, 5 and 6, is formed by an axial counterbore located within lower member 12. The coupon is mounted within chamber 44 where it is protected against abrasion and other damage while it is being lowered into the borehole.

In FIG. 5, the insulator 30 is provided with a threaded support end 46 that is opposed to lower terminal end 48 of coupon 32. The coupon 32 is solid metal and can be made of various compositions, but preferably, is made of 1010 or 1018 steel alloy. The metallic composition of the coupon is selected according to the production history of the well. The configuration of the coupon and the composition of the metallic alloy thereof can be adjusted while remaining within the scope of the present invention.

In FIGS. 2 and 5, upper body member 14 has opposed shoulders 50 and 52. Shoulder 50 abuttingly engages a sucker rod coupling, and shoulder 52 abuttingly engages shoulder 53 of the lower body member 12. Shoulder 54 of upper body member 14 abuttingly engages shoulder 56 of insulator 30, while shoulder 25 of lower body member 12 engages the exposed face formed on the boss of the insulator. Radial fluid flow ports 22 are each oblated and have a longitudinal axis arranged parallel to the longitudinal central axis of the main body members 12 and 14. The radial fluid flow ports 22 have a lateral axis arranged perpendicular to the longitudinal central axis of the main body. Therefore, chamber 44 and fluid flow ports 22 are parallel to one another and provide a means by which fluid can be exchanged between chamber 44 and the wellbore.

As shown in FIG. 5, numeral 58 indicates the upper end of one of the fluid flow ports 22. Each fluid flow port 22 communicates directly with chamber 44 which extends, as seen at 60, from shoulder 54 of the upper body member 14 towards the lower end 45 of chamber 44. The lower marginal end 62 of the fluid flow ports 22 is sloped in an outward and downward direction for reasons that will become more apparent later on in this disclosure.

In the embodiment shown in FIG. 7, apparatus 110 of this invention has an upper body member 114 that has been provided with a fishing neck 64 rigidly attached thereto. The fishing neck 64 is of conventional design and can be latched onto by a number of different well known fishing tools. The lower body member 112 has a lower marginal end 117 thereof configured for accepting a fishing neck 66 that may be attached to the upper end 68 of a prior art downhole pump, for example. This arrangement mounts the corrosion test coupon holder apparatus 110 on top of a prior art downhole hydraulically actuated pump 68 of the free type, for example.

In the embodiment of FIG. 8, the coupon holding apparatus 210 of this invention has a lower body member 212 connected to an upper body member 214 in the before described manner, with opposed marginal ends thereof having female threads 120 and 118 formed therein for connection to the male ends of an apparatus, as for example, a sucker rod of a rod string. This configuration of the invention provides apparatus 210 with opposed threaded ends that can be directly attached within a string of sucker rod, in the same manner as a sucker rod coupling.

In FIG. 2, the opposed threaded connections 18 and 20 are shown as pin ends; and, as box ends 118 and 120 in FIG. 8. The opposed ends can also be made a pin and box, or a box and pin, as may be desired.

In operation, the coupon holder apparatus 10 of the present invention is threadedly made up in series relationship respective to a string of sucker rod. Apparatus 10 preferably is located in close proximity to a downhole pump so that the rate of corrosion of the downhole equipment can be measured and thereby provide data related to the quantity of inhibitor that must be injected periodically into the wellbore in order to inhibit corrosion of the downhole production equipment.

As seen in FIG. 1, as a rod string reciprocates the downhole pump, the coupon holder apparatus 10 of the present invention reciprocates therewith, and accordingly, on the downstroke the apparatus 10 passes through a column of fluid contained within the tubing string; and, on the upstroke, the produced fluid is lifted concurrently with the apparatus 10 and relative velocity therebetween is considered almost zero.

On the downstroke, fluid enters each of the radial fluid flow ports 22 as indicated in FIG. 6. Any debris entering chamber 44 or the fluid flow ports 22 is swept out of the outwardly and downwardly sloped lower marginal end 62 of the ports 22. The passage of fluid across the ports each alternate stroke of the pump induces a flow into the upper part of chamber 44, and thereby continually changes the fluid through radial fluid flow ports 22 and chamber 44. Consequently, this brings about a situation wherein a representative sample of the downhole fluid is placed in intimate contact with test coupon 32. The coupon 32 extends from the upper end of chamber 44, which is defined by shoulder 54 of upper body member 14, along the longitudinal axial centerline of the chamber 44, with the lower terminal end 48 of the coupon terminating short of lower end 45 of chamber 44.

From time to time, it is necessary to pull the pump and the rod string for one reason or another, whereupon the apparatus 10 is removed from the sucker rod string at that time and another new apparatus 10 substituted therefor. The removed apparatus 10 is sent to the lab where a technician removes coupon 32 therefrom for analysis.

By comparing the rate of reaction of the metallic alloy of coupon 32 with the rate of production that was recorded for the well, the technician can make the necessary changes in the quantity and type of inhibitor being injected into the wellbore for corrosion protection.

Accordingly, the present invention provides a method and apparatus for measuring the rate of corrosion downhole in a borehole by the provision of a coupon holder suspended within a chamber of the holder which is attached in series relationship respective to a sucker rod string. This disposes the coupon in close proximity to the fluid produced by the downhole pump, and provides corrosion analysis of the formation fluid that flows into the bottom of a wellbore in a new and unobvious manner heretofore unknown to those skilled in the art.

I claim:

1. In a wellbore having a downhole pump at the lower end of a production tubing string, a sucker rod string positioned within a production tubing and connected to reciprocate the downhole pump, the combination with said sucker rod string of an apparatus for measuring the rate of corrosion downhole in the borehole; said apparatus comprising a main body having opposed ends, means for forming a connection at said opposed ends by which said main body is series connected within the rod string to thereby suspend the apparatus downhole in the borehole, and further comprising;

an axial chamber formed by an interior wall surface in said main body; radial ports extending through a sidewall of said main body and communicating said axial chamber with the exterior of said main body; a corrodible test coupon mounted within said chamber and extending along the central longitudinal axis thereof; insulating means by which said coupon is insulated from said main body and by which said coupon is spaced from said interior wall surface of said chamber to place said coupon in intimate contact with produced well fluid;

wherein, said radial ports are oblated and include a lower curved end which is sloped downwardly and outwardly with respect to said longitudinal axis whereby reciprocation of the apparatus forces well fluid to flow through said chamber into contact with said coupon;

said main body being comprised of an upper member and a lower member; means threadedly attaching said upper and lower members together in a removable manner; said chamber being a bore formed in said lower member;

said insulating means being mounted to an end wall of the upper member, said end wall also defining the upper end of the chamber, said coupon extending downwardly into the bore formed in the lower member;

whereby well fluid makes contact with the coupon and the coupon reacts with the well fluid, and the rate of reaction between the coupon and the well fluid provides an indication of the rate of corrosion.

2. The combination of claim 1 wherein the insulating means has a boss formed thereon; said upper member receives said insulating means axially, and said coupon is supported by said insulating means and extends downhole from the insulating means along the central axis of the chamber;

said upper and lower members having spaced confronting shoulders that abuttingly engage opposed faces of said boss.

3. The combination of claim 1 wherein the main body is cylindrical and has opposed male threaded ends and said coupon is of cylindrical configuration.

4. In a borehole having a rod actuated downhole pump located at the lower end of a production tubing and a rod in said production tubing for actuating said pump, the combination with said rod of a coupon holder for measuring the rate of corrosion downhole in the borehole; said coupon holder comprising a main body having opposed ends by which said main body is series connected within the rod which is attached to the downhole pump which is suspended downhole in the borehole, and further comprising;

said main body being an elongated cylinder; an axial chamber formed by an interior wall surface within said main body; spaced radial ports extending through a sidewall of said main body and communicating said axial chamber with ambient; said spaced radial ports being circumferentially disposed about the axial chamber and oblated to present a lower curved end opposed to an upper curved end;

an insulator, means for mounting said insulator at one end of said chamber; a corrodible test coupon mounted within said chamber, means by which said coupon is supported by said insulator wherein said coupon is insulated from said interior wall surface;

wherein the insulator has a boss formed thereon, said main body is made of upper and lower members affixed to one another; said upper member receives said insulator axially, and said coupon is supported by said insulator and extends along the central longitudinal axis of the chamber;

said upper and lower members having spaced confronting shoulders that abuttingly engage opposed faces of said boss; said lower curved end of each port being sloped downwardly and outwardly with respect to said longitudinal axis whereby reciprocation of the coupon holder forces well fluid to flow through said chamber;

whereby, well fluid makes contact with said coupon and the coupon reacts with the well fluid, and the rate of reaction between the coupon and the well fluid provides an indication of the corrosion rate.

5. The combination of claim 4 wherein a bore is formed in said lower body member to form said chamber, and further comprising; thread means for attaching the upper and lower body members together in a removable manner and;

means mounting said coupon to said insulator; means mounting said insulator to an end wall of the upper member to extend the coupon into the bore in the lower member; an annular shoulder on said upper member, an annular shoulder on said lower member; said upper and lower annular shoulders engaging said opposed faces of the boss.

6. The combination of claim 5 wherein the oblated ports have a longitudinal length that is parallel to the longitudinal axis of the chamber and are aligned on opposed sides of the coupon; the lower end of said port being sloped so that debris flowing into said chamber gravitate away from said coupon.

7. In a pumping unit having a pump located in a borehole and a sucker rod string extending downhole through a tubing string to actuate the pump, the combination with said rod string of a coupon holder apparatus for measuring the corrosive properties of the fluid contained downhole in the borehole wherein;

said coupon holder apparatus for measuring the rate of corrosion downhole in a borehole includes a main body; said main body has opposed ends by which said main body is connected within and forms part of said rod string and is thereby suspended down hole in the borehole in series relationship respective to the rod-string and supports part of the downhole pump, and comprising;

an axial chamber in said main body formed by an interior wall surface; radical ports extending through a sidewall of said main body and communicating said axial chamber with the exterior of said main body;

a corrodible test coupon, means by which said coupon is mounted within said chamber; means for insulating said coupon from the interior wall surface that forms said chamber;

said main body being comprised of an upper member and a lower member; means threadedly attaching said upper and lower members together in a removable manner;

wherein, said means for insulating is an insulator and said coupon is supported therefrom; said insulator has a boss formed thereon and is mounted to an end wall of the upper member and extends into the chamber, said chamber being located in the lower member, wherein an outer face of the boss is placed closely adjacent to an upper annular face of the lower member;

whereby; well fluid makes contact with said coupon, and the coupon reacts with the well fluid, so that the rate of reaction between the coupon and the well fluid is an indication of the rate of corrosion.

8. The combination of claim 7 and further comprising means for threadedly attaching said upper and lower members together in an axially aligned and a removable manner; said lower member having a counterbore formed therein that provides said chamber;

means for mounting said coupon in said insulator; wherein said insulator is non-metallic and is mounted to an end wall of the upper member, and said coupon extends downwardly into the chamber of the lower member.

9. The combination of claim 8 wherein said upper member threadedly receives said insulator axially, and said coupon is a rod that extends along the central axis of said chamber; said radial ports are oblated and include a lower end which is curved and sloped downwardly and outwardly with respect to the central longitudinal axis of said chamber whereby debris gravitates from said chamber.

10. The combination of claim 9 wherein the main body is cylindrical and has opposed male threaded ends; the upper member is cylindrical and has opposed male threaded ends; the lower member is cylindrical and has an upper female threaded end opposed to a lower male threaded end.

11. The combination of claim 10 wherein the oblated ports have a longitudinal length that is parallel to the longitudinal axis of said chamber; and the lower sloped end of said port is arranged at about 30 degrees to the horizontal.

12. The combination of claim 11 wherein said coupon is made from a metal alloy that reacts with well fluids at a rate which consumes the coupon over a time interval that allows the rate of corrosion to be evaluated.

13. The combination of claim 9 wherein said lower member has a fishing neck formed in the lower marginal end thereof by which said holder is removably attached to the upper end of said pump.

14. The combination of claim 9 wherein said main body has opposed female threads by which said coupon holder is connected in said rod string.

15. The combination of claim 9 wherein said main body has an upper male thread and a lower female thread by which the main body connects said rod string to the upper end of said downhole pump.

* * * * *